United States Patent
Schilling et al.

(10) Patent No.: US 9,434,755 B2
(45) Date of Patent: Sep. 6, 2016

(54) PROCESS FOR THE ISOLATION OF RHAMNOLIPIDS

(71) Applicants: Martin Schilling, Bonn (DE); Marius Ruetering, Meschede (DE); Verena Dahl, Cologne (DE); Fabien Cabirol, Essen (DE)

(72) Inventors: Martin Schilling, Bonn (DE); Marius Ruetering, Meschede (DE); Verena Dahl, Cologne (DE); Fabien Cabirol, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 221 days.

(21) Appl. No.: 14/089,168

(22) Filed: Nov. 25, 2013

(65) Prior Publication Data
US 2014/0148588 A1 May 29, 2014

(30) Foreign Application Priority Data

Nov. 26, 2012 (DE) .......................... 10 2012 221 519

(51) Int. Cl.
  *C07H 15/04* (2006.01)
  *C11B 1/10* (2006.01)
(52) U.S. Cl.
  CPC ................ *C07H 15/04* (2013.01); *C11B 1/10* (2013.01); *C11B 1/108* (2013.01)
(58) Field of Classification Search
  None
  See application file for complete search history.

(56) References Cited

U.S. PATENT DOCUMENTS

| | | | |
|---|---|---|---|
| 4,814,272 A * | 3/1989 | Wagner et al. ................. | 435/74 |
| 5,466,675 A | 11/1995 | Piljac et al. | |
| 2012/0220464 A1 | 8/2012 | Giessler-Blank et al. | |

FOREIGN PATENT DOCUMENTS

| | | |
|---|---|---|
| WO | WO 93/14767 A2 | 8/1993 |
| WO | WO2012013554 | 2/2012 |

OTHER PUBLICATIONS

Pinzon, N. M., & Ju, L. K. (2009). Analysis of rhamnolipid biosurfactants by methylene blue complexation. Applied microbiology and biotechnology, 82(5), 975-981.*
Pornsunthorntawee, O., Wongpanit, P., Chavadej, S., Abe, M., & Rujiravanit, R. (2008). Structural and physicochemical characterization of crude biosurfactant produced by *Pseudomonas aeruginosa* SP4 isolated from petroleum-contaminated soil. Bioresource Technology, 99(6), 1589-1595.*
Haynes, W. M. (Ed.). (2015). CRC handbook of chemistry and physics, 96th Edition. CRC press. retrieved from http://www.hbcpnetbase.com/.*
Sarachat, T. et al., "Purification and concentration of a rhamnolipid biosurfactant produced by *Pseudomonas aeruginosa* SP4 using foam fractionation", Bioresource Technology 101, Jan. 2010, pp. 324-330.
Abdel-Mouwgoud, A.M. et al., Characterization of Rhamnolipid Produced by *Pseudomonas aeruginosa* Isolate Bs20, Appl Biochem Biotechnol, (2009), vol. 157, pp. 329-345.
Rooney, A.P. et al., Isolation and Characterization of Rhamnolipid-Producing Bacterial Strains From a Biodiesel Facility, FEMS Microbiol Lett, (Jun. 1, 2009), vol. 295, pp. 82-87.

* cited by examiner

*Primary Examiner* — Eric Olson
*Assistant Examiner* — Dale R Miller
(74) *Attorney, Agent, or Firm* — Scully, Scott, Murphy & Presser, P.C.

(57) ABSTRACT

A process for isolating rhamnolipids is provided. The process includes providing an aqueous medium containing at least one rhamnolipid and having a pH of less than 6. Next, the aqueous medium is brought into contact with at least one organic solvent to provide a multiphase system and then the aqueous phase is separated off. The pH is then increased to a value of 6 or more to provide a multiphase organic system. Next, a rhamnolipid-enriched organic phase is separated off. An optional step of further purifying the rhamnolipid may be performed.

9 Claims, No Drawings

PROCESS FOR THE ISOLATION OF RHAMNOLIPIDS

FIELD OF THE INVENTION

The present invention relates to a process for the isolation of rhamnolipids.

PRIOR ART

Rhamnolipids are interface-active glycolipids and metabolic products of certain microorganisms, the best known producer of which is probably *Pseudomonas aeruginosa*.

Rhamnolipids have particular surface-active properties such as, for example, a strong foaming ability, and are of interest for highly diverse technical applications.

Since rhamnolipids can be prepared under mild conditions by means of fermentation based on renewable raw materials, rhamnolipids fit well with the contemporary megatrend of "sustainability" and "green chemistry". As such, the interest in rhamnolipids has increased steadily in recent years.

However, rhamnolipids have only been available on the market in small amounts and at high prices and can only compete with the chemical-synthetic surfactants typically used in, for example, body care products and household cleaners in niche applications. One reason for the high costs is the difficult work-up of the fermentation product from the fermentation broths, which contain a large number of contaminating secondary components. These include incompletely reacted lipophilic and amphiphilic substrates (e.g., tri- and partial glycerides and also fatty acids), lipophilic and amphiphilic cell constituents (e.g., phospholipids of the cell membranes), and also antifoams (e.g., silicone-, vegetable oil- or polyether-based), which are used for foam control during the fermentation.

Antifoams are troublesome in the subsequent application and, on account of the amphiphilic nature of the rhamnolipids, can only be separated off from the rhamnolipids with difficulty. Besides the foam-inhibiting components, in many cases hydrophilic fermentation by-products, such as e.g., proteins and microbial polysaccharides, also have to be separated off since these may be troublesome for other reasons in the end product (microbial stability, toxicological properties etc.). Finally, during the work-up, a strong concentration of the aqueous RL (i.e., rhamnolipid) solution must also be achieved since surfactant solutions are required, on the marketing side, in as highly concentrated a form as possible. For ecological reasons, the smallest possible amounts of water should be transported with the product in order to ensure the lowest possible fuel consumption per kg of active substance. The product concentrations that can be achieved by fermentation are relatively low; hitherto no concentrations greater than 100 g/l are known from the literature.

The literature discloses a number of methods of purifying rhamnolipids, which are often a mixture of different forms (e.g., mono- and di-rhamnolipids), and of separating them from the aforementioned impurities.

Various technically demanding methods in terms of processing, such as e.g., the use of membrane filtration, adsorption onto ion exchangers, and foam fractionation during fermentation permit partial purification, however neither the hydrophilic nor the hydrophobic impurities can be separated off to an adequate degree by any one of these process steps. Moreover, a cost-efficient use on an industrial scale for the purification of RLs has not been investigated and tends to be too expensive in order to be able to compete with the classic chemical-synthetic surfactants as regards production costs. This is also true for the available chromatographic processes.

Sarachat et al. (2010) describe the acidic extraction of fermentation broths with an organic solvent or solvent mixture of average polarity, such as e.g., ethyl acetate, chloroform-methanol, chloroform-ethanol or dichloromethane, in which lipophilic components are firstly co-extracted. The rhamnolipids are precipitated, with cooling, and further purified in a second step by means of stepwise addition of a nonpolar solvent, such as, for example, hexane or chloroform.

It is an obvious disadvantage of this process that the addition of toxicologically unacceptable, petroleum-based nonpolar solvents such as hexane or chloroform and a crystallization step with cooling are required. Besides the higher costs, and the technical requirements in terms of processing and safety, such a process is also not ideal in the spirit of sustainable, green chemistry. Moreover, there are already now regulatory requirements which do not permit the ecological certification and marketing of a product originating from such a process.

SUMMARY OF THE INVENTION

The present invention provides a process for the purification of rhamnolipids which is able to overcome at least one of the disadvantages of the prior art.

In some embodiments of the present invention, it is an advantage of the process according to the invention that less solvent is used.

In other embodiments of the present invention, it is a further advantage that the solvents used in the process of the present invention are acceptable in terms of toxicology and safety.

In still other embodiments of the present invention, it is a further advantage that solvents originating from sustainable sources can be used.

In further embodiments of the present invention, it is a further advantage that the process according to the invention can be carried out at energetically favorable temperatures.

In still further embodiments of the present invention, it is a further advantage that the process according to the invention can be carried out with simple technical equipment.

In some embodiments, the process according to the invention can permit the purification/concentration of large amounts of product within a very short time.

In yet other embodiments of the present invention, it is also an advantage that in the process according to the invention the concentrated and purified product is not obtained as a solid, but as a liquid phase, which facilitates further processing in technical terms. The highly concentrated solution produced constitutes the finished end product.

In some embodiments of the present invention, the process according to the invention is suitable for working up both fermentation broths and also already partly purified rhamnolipids.

The process according to the invention for the isolation of rhamnolipids comprises:

A) providing an aqueous medium containing at least one rhamnolipid and having a pH of less than 6, in particular less than 5, B) bringing the aqueous medium into contact with at least one organic solvent to provide a multiphase system and separating off the aqueous phase, C) increasing the pH to a value of 6 or more to provide a multiphase organic system, D) separating off a rhamnolipid-enriched organic phase, and E) optionally further purifying the rhamnolipid.

DETAILED DESCRIPTION OF THE INVENTION

The present invention, which discloses a process for the isolation of rhamnolipids will now be described in greater detail.

In connection with the present invention, the term "rhamnolipid" is to be understood as meaning compounds of general formula (I) or salts thereof,

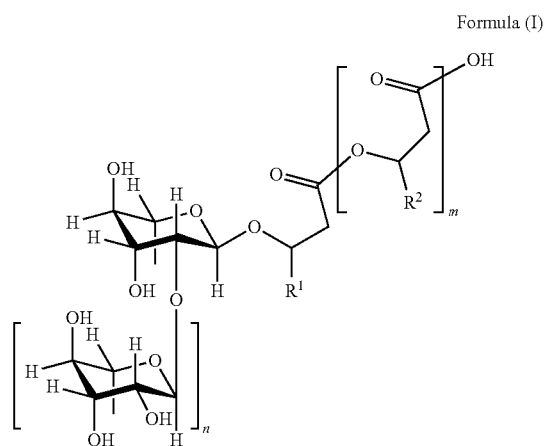

Formula (I)

where m=2, 1 or 0, in particular 1 or 0, n=1 or 0, in particular 1, $R^1$ and $R^2$=independently of one another identical or different organic radical with 2 to 24, preferably 5 to 13, carbon atoms, in particular optionally branched, optionally substituted, in particular hydroxy-substituted, optionally unsaturated, in particular optionally mono-, di- or triunsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12.

The "pH" in connection with the present invention is defined as the value which is measured for corresponding substance at 25° C. after stirring for five minutes using a pH electrode calibrated in accordance with ISO 4319 (1977).

In connection with the present invention, the term "aqueous medium" is to be understood as meaning a composition which comprises at least 5% by weight of water, based on the total composition under consideration.

Unless stated otherwise, all of the stated percentages (%) are percentages by mass.

In some embodiments of the present invention it is preferred that the total aqueous medium in process step A) of the present invention comprises between 10 g/l and 300 g/l, in particular between 50 g/l and 150 g/l, rhamnolipids, the litre data referring to the total aqueous medium.

In some embodiments of the present invention, the aqueous medium in process step A) is preferably a cell-free or cell-containing fermentation broth, preferably a cell-free one.

In particular, the process according to the invention is characterized in that the aqueous medium in process step A) has a pH of from 2 to 4.5, in particular from 3.5 to 4. The pH can be adjusted using an acid, in particular an inorganic acid, which is preferably selected from HCl, $H_2SO_4$, nitric acid, phosphoric acid, carbonic acid, and is in particular HCl.

It is advantageous for the process according to the invention if, after process step D), a certain amount of water is present in the rhamnolipid-enriched organic phase; this has the technical effect that by simply removing, for example distilling off, the organic solvent, a highly concentrated, aqueous rhamnolipid fraction can be obtained; consequently, a preferred process according to the invention is characterized in that the organic solvent or the mixture of organic solvents of process step B) is able to dissolve water in an amount of from 0.1 to 30% by weight, preferably 0.5 to 7% by weight, where the percentages by weight refer to the sum of organic solvent and water.

Preferred organic solvents of process step B) are selected from methyl acetate, ethyl acetate, propyl acetate, isopropyl acetate, butyl acetate, isoamyl acetate, butan-1-ol, butan-2-ol and diethyl ether, with ethyl acetate being particularly preferred.

In some embodiments of the present invention it is preferred that the volume ratio at 20° C. of aqueous medium to organic solvent or to the mixture of organic solvents prior to bringing them into contact is from 0.2:1 to 5:1, preferably from 2:1 to 4:1 and more preferably from 2.9:1 to 3.1:1.

A preferred embodiment of the process according to the invention is characterized in that, in process step C), the pH is increased to 6.1 to 9, preferably to 6.5 to 8, more preferably to 6.9 to 7.1.

In some embodiments of the present invention, it is preferred that in process step C), the pH is increased by means of an inorganic base, in particular alkaline earth metal base, alkali metal base, preferably aqueous, or ammonia, with NaOH and KOH being more preferred.

One advantage of the process according to the invention is that it can be carried out for the large part at ambient temperature, thus process steps B), C) and D) can be carried out in a temperature range from 10 to 50° C., preferably 15 to 30, more preferably 18 to 25.

In process step E), the rhamnolipid can be further purified as required. A preferred embodiment of the process according to the invention is characterized in that, in process steps E), any organic solvent that is present is separated off from the rhamnolipid by means of at least partial evaporation. In this connection, it is preferred that the evaporation of the organic solvent is carried out under reduced pressure and at elevated temperature. In particular, a pressure range from 0.01 to 1 bar, preferably from 0.15 to 0.3 bar, in conjunction with a temperature of from 20 to 80° C., preferably from 40 to 60° C., has proven to be advantageous.

The process according to the invention can comprise a further process step F) which involves recovering any antifoam agent present, in particular from the organic phases. This can then be advantageously reutilized in a subsequent fermentation.

The examples listed below describe the present invention by way of example without intending to limit the invention, the scope of application of which arises from the description and the claims in their totality, to the embodiments specified in the examples.

EXAMPLES

Example 1

Separation and Concentration of Rhamnolipids from a Rhamnolipid/Fatty Acid Mixture by Means of Extraction and Ph-Induced Phase Separation

The starting material used for the purification and concentration described below was a rhamnolipid crude product produced by fermentation. This consisted to about 50% of various rhamnolipids, and to circa 20% of various fatty-acid-like impurities which were either introduced by the fermentation substrate or else were formed as by-product during the fermentation. These are primarily C10 hydroxy fatty acids and their dimers and monounsaturated C12 fatty acids. To detect the impurities in all preparation steps, a thin layer chromatographic method developed specifically for this purpose was used inter alia. The purification of rhamnolipids was carried out starting from an aqueous solution with an RL concentration of 50 g/l. The fraction of fatty acids in the aqueous solution was 20 g/l.

The fermentation broths and partially purified crude products often contain proteins which hinder the phase separation after extraction and lead to the formation of large interphases. In most cases, a product or yield loss is also associated with this. In order to prevent this, the proteins were hydrolyzed firstly by adding 1% by weight of a commercial protease preparation (alkalase, novozymes) at a pH=7 and 60° C. The subsequent extraction was considerably simplified as a result. To extract the rhamnolipids, the aqueous solution was adjusted to a pH of 4.0 with the help of concentrated HCl. Extraction was then carried out with the same volume of ethyl acetate. Phase separation in the separating funnel following successful extraction was carried out rapidly and reliably at room temperature (25° C.).

Hydrophilic impurities remain in the aqueous phase in this step. The more lipophilic impurities and almost 100% of the rhamnolipids present dissolved in the organic phase.

The rhamnolipid-containing organic phase was separated off and further processed. By adding 50% strength KOH (aq), the pH of the solution was adjusted to pH 7. A sudden onset of clouding of the solution within this pH range indicated the formation of a further organic phase; the organic phases were again separated in the separating funnel rapidly and without complication at room temperature (25° C.), the rhamnolipids becoming enriched primarily in the lower phase and the lipophilic impurities remaining for the greatest part in the upper phase.

Consequently, not only was a considerable concentration of the rhamnolipids achieved, but at the same time also effective purification of the same. After separating off the lower phase containing rhamnolipids, the organic solvent was stripped off by means of simple distillation at 0.2 bar and 60° C.

The rhamnolipid fraction obtained had a concentration of 500 g/l.

The purity was 80%. This corresponds to a 10-fold concentration with a purification factor of 1.6 for an overall 95% yield.

The finished end product had significantly better application properties than the contaminated starting solution. In particular, the foam properties were improved as a result. This was analyzed using a foam tester from SITA (R-2000). The purified product exhibited significantly more rapid foam formation kinetics and the achieved foam volume was likewise significantly higher.

Example 2

Separation and Concentration of Rhamnolipids from a Rhamnolipid/Antifoam Mixture by Means of Extraction and Ph-Induced Phase Separation

To separate off antifoam from a rhamnolipid solution, a commercially available rhamnolipid mixture (JBR 505) from Jeneil Biosurfactants was used.

The purification of rhamnolipids was carried out starting from an aqueous solution with a concentration of 50 g/l. The silicone-containing DOW Corning 1500 antifoam was added in an end concentration of 20 g/l.

To extract the rhamnolipids, the aqueous solution was adjusted to a pH of 4.0 with the help of concentrated HCl. Extraction was then carried out with the same volume of ethyl acetate. Phase separation in the separating funnel following successful extraction was carried out rapidly and reliably at room temperature (25° C.).

Hydrophilic impurities remain in the aqueous phase in this step. The more lipophilic impurities and almost 100% of the rhamnolipids present dissolved in the organic phase.

The rhamnolipid-containing organic phase was separated off and further processed. By adding 50% strength KOH (aq), the pH of the solution was adjusted to pH 7. A sudden onset of clouding of the solution within this pH range indicated the formation of a further organic phase; the organic phases were again separated in the separating funnel rapidly and without complication at room temperature (25° C.), with the rhamnolipids becoming enriched primarily in the lower phase and the majority of the lipophilic impurities as well as almost 100% of the antifoam remaining in the upper phase.

Consequently, as well as the purification and considerable concentration of the rhamnolipids, an effective separation off of the antifoam was also achieved at the same time. The separation off of the antifoam was demonstrated by means of quantitative $^1$H-NMR analysis. The signal typical of the polydimethylsiloxane antifoam at a chemical shift of about −0.1 ppm could no longer be detected in practice in the lower rhamnolipid-containing phase, but instead considerably in the upper ethyl acetate phase. After separating off the lower rhamnolipid-containing phase, the organic solvent was stripped off by means of simple distillation at 0.2 bar and 60° C.

The resulting rhamnolipid fraction had a concentration of 450 g/l.

The purity was 75%. This corresponds to a 9-fold concentration with a purification factor of 1.5 for an overall 90% yield.

The finished end product had considerably better application properties than the unpurified starting solution.

Example 3

Separation and Concentration of Rhamnolipids From a Fermentation Broth Containing Rhamnolipid and Antifoam

A fermentation with a *Pseudomonas putida* strain containing the rhamnolipid biosynthesis genes RhlA, RhlB and RhlC was carried out. The preculture in the shake flask was carried out as described in WO 2012013554 A1. A mineral medium (M9) was used for the main culture. The fermentation was conducted in a 2 litre fermenter under carbon-limiting conditions achieved via glucose feeding. The glucose feeding took place by reference to the dissolved oxygen signal. The dissolved oxygen was regulated via the stirrer speed at 20% saturation. The pH was regulated to 7 via a pH electrode and by adding NH$_4$SO$_4$. In order to prevent excessive foaming of the fermentation broth, in one case the silicone-containing antifoam DOW Corning 1500 was metered in, and in another case a sunflower oil was metered in. The fermentation was conducted over 4 days to a biodry mass of 15 g/l. The rhamnolipid concentration was ascertained by HPLC and is 9.8 g/l. The broth obtained at the end of the fermentation exhibits a strong tendency towards foaming neither in the case of the DOW Corning 1500 antifoam used, nor in the case of the sunflower oil. After separating off the cells by means of centrifugation at 10 000 g and subsequent precipitation of the rhamnolipids by acidification to pH=4, the rhamnolipid-containing lower phase was separated off and washed several times with water at pH=4. The resulting product was adjusted again to pH=7 by adding NaOH, at which the precipitated rhamnolipids dissolve again. The product obtained in this way has unfavorable application properties. The foam formation kinetics analyzed by means of a SITA measurement and the attained total foam volume are not sufficient. In contrast to this, a product with exceptional application properties, in particular exceptional foam properties, is obtained via the process claimed here.

Here, the extraction step and the subsequent concentration were carried out as in the examples described above. This can take place either directly from the cell-containing fermentation broth, or after separating off the cells. If the cells are not separated off, the phase separation proceeds significantly more slowly and a cell- and product-containing intermediate phase is formed, as a result of which the yield was reduced, but the purity and the application properties are not influenced. The DOW Corning 1500 antifoam and the sunflower oil can still be detected in traces in the resulting product via $^1$H-NMR. The majority remains in the upper organic phase and, after removing the solvent, can optionally be used in a further fermentation.

What is claimed is:

1. A process for the isolation of rhamnolipids, said process comprising:
   A) providing an aqueous medium containing at least one rhamnolipid and having a pH of less than 6, wherein the aqueous medium comprises between 10 g/l and 300 g/l of the at least one rhamnolipid,
   B) i) bringing the aqueous medium into contact with at least one organic solvent to provide a multiphase system X, wherein the at least one organic solvent dissolved in the aqueous medium is in an amount from 0.1 to 30% by weight of the multiphase system X, ii) separating off the aqueous phase from multiphase system X, to provide an organic phase Y,
   C) increasing the pH of the organic phase Y, to a value of 6 or more to provide a multiphase system Z comprising at least two organic phases, and
   D) separating off a rhamnolipid-enriched organic phase from the multiphase system Z.

2. The process according to claim 1, wherein said pH of said aqueous medium in process step A) is from 2 to 4.5.

3. The process according to claim 1, wherein the at least one organic solvent of process step B) is selected from methyl acetate, ethyl acetate, propyl acetate, isopropyl acetate, butyl acetate, isoamyl acetate, butan-1-ol, butan-2-ol and diethyl ether.

4. The process according to claim 1, wherein a volume ratio of the aqueous medium to the at least one organic solvent prior to bringing them into contact is from 0.2:1 to 5:1.

5. The process according to claim 1, wherein in process step C) the pH is increased to 6.1 to 9.

6. The process according to claim 1, wherein in process step C) the pH is increased by means of an inorganic base.

7. The process according to claim 1, wherein process steps B), C) and D) are carried out in a temperature range from 10 to 50° C.

8. The process according to claim 1, further comprising:
   E) further purify the rhamnolipid within the rhamnolipid-rich phase.

9. The process according to claim 8, wherein an organic solvent is used in process step E) to separated off from the rhamnolipid by means of at least partial evaporation.

* * * * *